United States Patent [19]

Wang

[11] Patent Number: 4,759,344

[45] Date of Patent: Jul. 26, 1988

[54] WANG'S TUBULES FOR SPERM PREPARATIONS USED FOR IVF-ET-GIFT AND ARTIFICIAL INSEMINATIONS

[76] Inventor: Fu-Nan Wang, 3527 Purdue Ave., Los Angeles, Calif. 90066

[21] Appl. No.: 856,659

[22] Filed: Aug. 11, 1986

[51] Int. Cl.⁴ .............................................. A61K 35/00
[52] U.S. Cl. ....................................... 128/1 R; 435/2
[58] Field of Search ......................... 128/1 R; 435/2; 424/105; 210/634; 422/99, 100, 102; 73/863.21

[56] References Cited

U.S. PATENT DOCUMENTS

| | | | |
|---|---|---|---|
| 4,009,260 | 2/1977 | Ericsson | 424/105 |
| 4,092,229 | 5/1978 | Bhattacharya | 128/1 R |
| 4,225,405 | 9/1980 | Lawson | 424/105 |
| 4,326,026 | 4/1982 | Sarkar | 435/2 |
| 4,474,875 | 10/1984 | Shrimpton | 435/2 |

Primary Examiner—Dalton L. Truluck
Assistant Examiner—Frank Wilkens
Attorney, Agent, or Firm—Lowe, Price, LeBlanc Becker & Shur

[57] ABSTRACT

A new method and apparatus is described for separating motile sperm from semen for use in fertilization. The semen sample is placed in communication with the inlet of a tubule filled with sperm media. The motile sperm then swim away from the semen through the tubule and are ultimately harvested. The sperms so collected are then separated from the semen which contains undesirable microorganisms, endotoxins, and the like.

9 Claims, 4 Drawing Sheets

WANG'S TUBULES FOR SPERM PREPARATIONS USED FOR IVF-ET-GIFT AND ARTIFICIAL INSEMINATIONS

BACKGROUND OF THE INVENTION

When performing artificial insemination procedures such as IU-AIH-/IU-AID (Intrauterine artificial insemination from husband/Intrauterine artificial insemination from donor) or IVF-ET-GIFT (In Vitro Fertilization Embryo Transfer, Gamete Intrafallopian Transfer) if raw semen is used, the embryo could be endangered. The semen invariably will contain microorganisms, and in addition, white corpuscles, and cellular debris, and when the microorganisms autolyze, endotoxins.

In an effort to prevent microorganisms from being introduced, antibiotics have been added to the sperm media or the embryo culture media. The antibiotics however are only effective against the live microorganisms and do not eliminate debris and endotoxins.

Accordingly, it is desirable to separate motile spermatozoa from semen to facilitate artificial insemination procedures without the introduction of substances which might put the embryo or the patient at risk.

SUMMARY OF THE INVENTION

It has now been discovered that when an aliquot of raw semen or washed semen pellet is placed in a tubule of this invention filled with sperm media such as B.W.W. media or Hams F-10 with ten percent preovulatory human serum, the sperm, or at least the most active sperm, will swim away from the specimen leaving behind debris, immobile sperm, endotoxins, microorganisms and the like. The sperm can then be collected for use in artificial inseminations or IVF-ET-GIFT in sufficient quantities to fertilize several eggs. The sperm sample then is free of microorganisms and other undesirable substances without the use of antibiotics or the introduction of any foreign substances into the sample. Furthermore, the sperms collected are the most motile as will be subsequently explained.

Accordingly, it is an object of this invention to separate motile sperm from semen for artificial insemination and IVF-ET-GIFT procedures.

It is an other object of this invention to provide a microorganism free sperm specimen without the use of antibiotics or the like.

It is yet another object of this invention to provide an apparatus for separating the most motile sperm from a semen specimen.

It is yet another object of this invention to provide a method for collecting a sperm containing specimen for a fertilization procedure which will consist of only the most motile sperm in a semen sample and which will not introduce microorganisms, endotoxins and the like from the semen specimen into the fertilization procedure.

BRIEF DESCRIPTION OF THE DRAWINGS

These and other objects will become readily apparent with reference to the drawings and following description wherein.

DETAILED DESCRIPTION OF THE INVENTION

Figure 1:
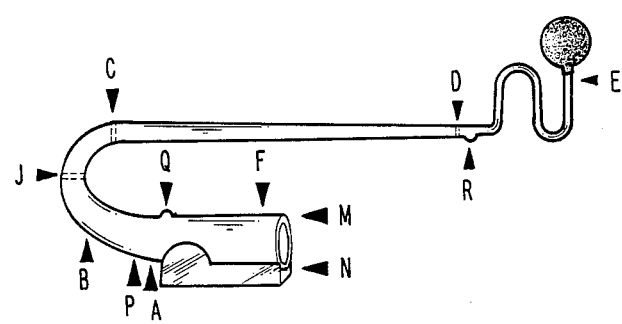
FIG. 1 is a side view of the duck like tubule embodiment of this invention.
Figure 1A:
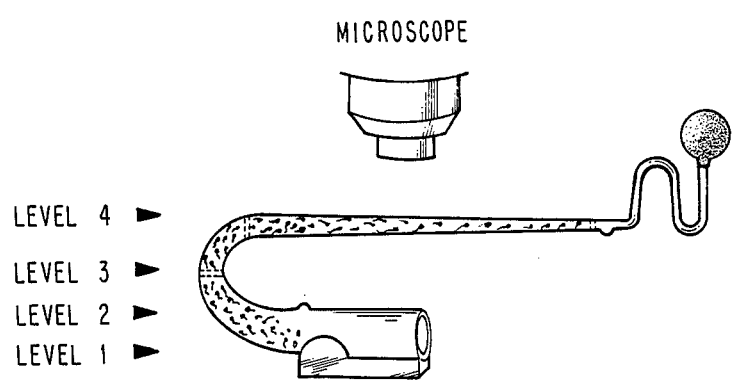
FIG. 1A is an illustration similar to FIG. 1 showing spermatozoa swimming through the duck-like tubule.

With attention to the embodiment of FIGS. 1 and 1A, the duck-like tubule is constructed of glass with a rubber bulb to be mounted at point E. Part H is a convex extension into the lumen of the tubule which serves to retain the sperm sample and media. Initially, a sperm media such as B.W.W. media or Ham's F-10 with ten percent preovulatory human serum is used to fill the hollow tubule from point A to point R with point F facing up and at an angle to the vertical. When the tubule is full the rubber bulb is then placed on point E and the tubule is returned to the position of FIGS. 1 and 1A resting on a support member G.

A sperm containing sample which may be either raw semen or a washed semen pellet is then placed at point A within the tubule, and incubate. The sample has a greater specific gravity than the media so it remains at point A. Bubble Q is disposed above point A for collecting any air which may be introduced with the sperm sample. The volume of bubble Q is 0.01 ml. The inner diameter at point F, i.e., the distance between M and N is 6 mm. The distance from point Q to point A is 6.1 mm. The tubule then gradually tapers along its length to point D and a sperm collection bubble R is provided for the most motile sperm. The bubble R has a volume of 0.01 mm. Score lines are provided at D, C, and J whereby segments of the tubule can be broken off so that the contents thereof may be analyzed. In the alternative, as shown in FIG. 1A, a microscope can be used directly to observe the sperm traveling for example from point C to point R through segment C-D.

The following are the volumes of the segments of the duck-like tubule of FIGS. 1 and 1A:

The volume from point P to point C is 0.15 ml.
The volume from point C to point D is 0.12 ml.
The volume from point D to point E is 0.06 ml.
The volume from point A to point P is 0.05 ml.
The volume of air in the collecting space Q is 0.01 ml.
The volume of the sperm collecting pool R is 0.1 ml.
The volume of the rubber bulb is 0.5 ml.

It should be noted that the volume of 0.15 ml from point P to point C is sufficient for the sperm to wash away the microorganisms which could adhere to the surface of the sperm in the original sample.

The following are segment lengths of the duck-like tubule of FIGS. 1 and 1A:

The length from point N to point B is 3 cm.
The length from point M to point L is 3 cm.
The length from point A to point B is 1 cm.
The length from point Q to point L is 1 cm.
The length along the outer surface from point B to point C is 2 cm.
The straight line length from point K to point L is 1 cm.
The length from point C to point D is 6 cm.
The length from point D to point E is 4 cm.
The length from point A to point D is 9 cm.

A U-shaped tubule portion is provided between points D and E to prevent microbes from the air contaminating the sperm.

The swimming speed for a sperm is about 25 um per second, i.e. 9 cm per hour. By using a microscope as shown in FIG. 1A a rough count of the number of sperm in the segment between point C and D can be made for example every half hour. When the number of sperm counted is sufficient for clinical use the tubule may be broken at points C and D. Sperm in the segment C-D is usually present in a concentration of $20-30 \times 10^6$/ml. The media containing sperm is removed from the tubule by squeezing the rubber bulb provided at E.

The tubule of this invention has been found to provide at harvest sufficient sperm to fertilize 10 to 50 eggs in an IVF-ET-GIFT program and with use of one to three such duck-like tubules sufficient for intrauterine inseminations, IU-AIH/IU-AID.

Samples were collected for testing by masturbation. The donor or husband was instructed after a three day period of continence to wash the glans penis and outer genital area with soap and water thoroughly twice before masturbation. As noted above, however, even after careful washes microorganisms and the like will be present in the semen sample.

Table I below is an analysis of the sperm present at levels 1, 2, 3 and 4 of FIG. 1A. Level 4 is the ultraqualified layer, (segment C-D).

TABLE 1

Characters of semen in duck-like tubule after swim-up.
semen in duck-like tubule after new swim-up

| | layer | | | |
|---|---|---|---|---|
| | 1 | 2 | 3 | 4 |
| | appearance | | | |
| CONTENT | gray-white color | marked turbid | moderate turbid | sl turbid or clear |
| particle | 3+ | — | — | — |
| debris | 3+ | 2+ | — | — |
| spermatid | 3+ | + | — | — |
| microbes | 3+ | + | — | — |
| W.B.C. | 3+ | + | — | — |
| dead/immobile sperm | 3+ | — | — | — |
| Gr.4 sperm | ± | + | 2+ | 3+ |
| Gr.3 sperm | + | 2+ | 3+ | + |
| Gr.2 sperm | 2+ | 3+ | 2+ | — |
| Gr.1 sperm | 3+ | 2+ | ± | — |

Figure 2:
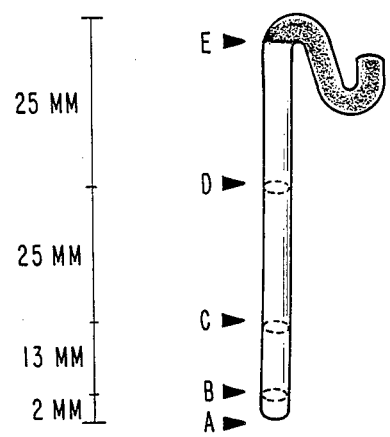
FIG. 2 is an illustration of the U-shaped tubule of this invention.
Figure 2A:
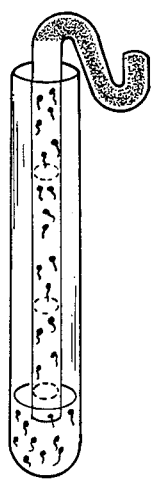
FIG. 2A is an illustration similar to FIG. 2 showing spermatozoa swimming upwardly through the tubule.

FIGS. 2 and 2A illustrate the U-shaped tubule embodiment of this invention. The tubule as has an inner diameter of 3.5 ml and a wall thickness of 0.5 ml or less. The length of each segmented tubule is as follows:
The length from point A to point B is 2 mm.
The length from point A to point C is 15 mm.
The length from point C to point D is 25 mm.
The length from point D to point E is 25 mm.
The length from point E to the distal end of the tubule is 25 mm.
The volume of each segment is as follows:
The volume from point A to point B is 0.02 ml.
The volume from point A to point C is 0.15 ml.
The volume from point C to point D is 0.25 ml.
The volume from point D to point E is 0.25 ml.
The segment from point E to the distal end of the tubule is solid.

Therefore the total volume of the U-shaped tubule is 0.65 ml.

The outer surface of the tubular wall is scored at points B, C, and D so that a segment may be broken and its contents analyzed.

To use the embodiment of FIGS. 2 and 2A, the tubule is initially filled with a sperm media from point A to point E as described above. A borosilicate test tube having a length of 75 mm in an inner diameter of 22 mm is provided. An aliquot of semen specimen is prepared at the bottom of the tube as shown in FIG. 2A. The tubule of this invention is then placed in the test tube as shown in FIG. 2A. As in the procedure described above, the sample is then incubated at a temperature of 37° C. in a high humidity and 5% carbon dioxide for about one hour.

After incubation, the tubule is broken at point C and point D and the samples from that segment and from the segment from point D to point E are analyzed. It was found that in a typical procedure the concentration of sperm from segment C-D is $6-12 \times 10^6$/ml with a volume of 0.25 ml. The sample from segment D-E contains $2-4 \times 10^6$/ml sperm with the volume of 0.25 ml. The sperm count in the C-D sample was found to be $20 \times 10^5$, and the sperm count in the D-E sample was $7.5 \times 10^5$. Both samples were found to be free of microorganisms. The C-D sample is sufficient quantity to fertilize 10-40 eggs and the D-E sample has a sperm count of sufficient concentration to fertilize 3-12 eggs.

Figure 3:
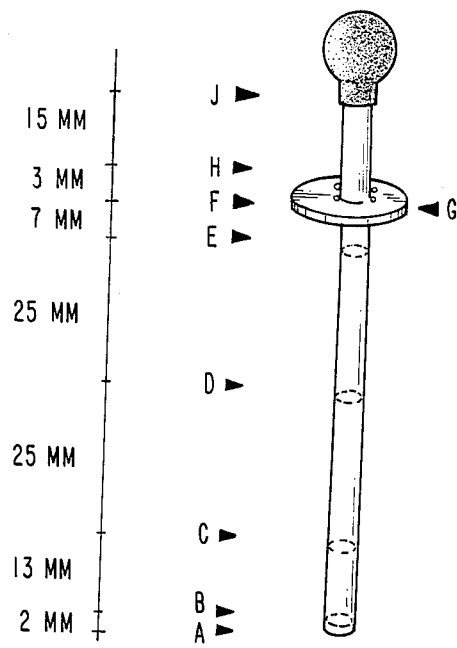
FIG. 3 is a illustration of the 4-pore tubule embodiment of this invention.
Figure 3A:
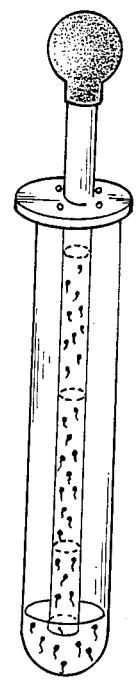
FIG. 3A is an illustration similar to FIG. 3 showing spermatozoa swimming upwardly through the 4-pore tubule.

With reference to the embodiment of FIGS. 3 and 3A, this embodiment consists of a tubule having an inner diameter of 3.5 ml and a wall thickness of 0.5 ml or less. The following are the segment lengths:
The length from point A to point B is 2 ml.
The length from point A to point C is 15 ml.
The length from point C to point D is 25 ml.
The length from point D to point E is 25 ml.
The length from point E to point F is 7 ml.
The thickness of the cover G is 3 ml and the diameter of G is 25 ml.
The diameter of each pore shown in G is 2 ml.
The length from point H to point J is 15 ml.
The length from point A to point F is 72 ml.
The total length of the glass tubule is 90 ml.
The volume of each segment is as follows:
The volume from point A to point B is 0.2 ml.
The volume from point A to point C is 0.15 ml.
The volume from point C to point D is 0.25 ml.
The volume from point D to point E is 0.25 ml.
The volume from point E to point F is 0.07 ml.
The volume from point F to point J is 0.18 ml.
The volume from point A to point F is 0.72 ml.
The volume of the rubber bulb is 0.65 ml.

The function of the pores in cover G is to permit carbon dioxide from the surrounding atmosphere to reach the semen sample. Carbon dioxide is a main energy source for the sperm.

The rubber bulb is used to fill the tubule with sperm medium. The bulb is squeezed and as it is released the medium enters the tubule at its orifice. The rubber bulb volume is equal to that volume of the segment from point A to point E.

Grasping the tubule between segments H and J the tubule is then placed in an aliquot of semen sample in a borosilicate test tube as shown in FIG. 3A. The sample is then incubated at a temperature of 37° with high humidity and an atmosphere of 5% carbon dioxide for one hour.

After incubation the tubule is broken at points C and D and the sample taken therefrom. The tubule is then broken at point E and the sample taken from that segment. The sample analysis was found to be equivalent to that presented above with reference to the embodiment of FIGS. 2 and 2A.

In summary, there is described herein an apparatus and method for separating the most motile sperm from a semen sample so that the sperm is available for fertilization without substances normally found in semen which could cause danger to the ambryo. In addition, the sperm sample of this invention is microorganism free without the use of an antibiotic.

It has been discovered that in a sperm media, sperm will swim away from the semen sample and within a short distance be free of microorganisms and any other undesirable debris. Swimming at a rate of about 9 cm an hour, in a tubule of this invention, after a predetermined period of incubation, the appropriate segments can be removed and their contents will provide microorganism free sperm in sufficient quantities for conventional fertilization procedures.

I claim:

1. A method for separating motile sperm from a semen specimen comprising the steps of:
   providing a hollow glass tubule having a predetermining length and an inlet end;
   filling said tubule with sperm media;
   providing a semen specimen;
   placing said specimen in communication with said media through said inlet;
   incubating said media and specimen for a predetermined period of time whereby motile sperm will swim away from said xpecimen and through said tubule;
   providing at least one score line around the outside surface of said tubule a perdetermined distance from said inlet and collecting said sperm by breaking said tubule along said score line and separating and collecting the contents thereof upstream of said score line.

2. The method of claim 1 wherein said tubule has an outlet and the step of filling said tubule comprises;
   providing a squeezable, hollow suction means at said outlet for sucking a predetermined quantity of media into said tubule through said inlet.

3. The method of claim 2 wherein said suction means comprises a rubber bulb.

4. The method of claim 1 wherein said tubule is cylindrical.

5. The method of claim 1 wherein said tubule is U-shaped along a substantial portion of the length thereof from the inlet.

6. The method of claim 5 the inlet is normally contained in a vertical plane during incubation and said tubule further comprises retaining means disposed therein adjacent the inlet for retaining media and specimen in said tubule during incubation.

7. The method of claim 6 wherein said tubule further comprises sperm collection means upstream of said inlet for collecting motile sperm.

8. The method of claim 1 wherein the step of incubating further comprises maintaining said tubule media and specimen at a temperature of about 37° C. in a humid atmosphere containing about 5% carbon dioxide.

9. The method of claim 8 wherein incubating is maintained for about one hour.

* * * * *

UNITED STATES PATENT AND TRADEMARK OFFICE
CERTIFICATE OF CORRECTION

PATENT NO. : 4,759,344
DATED : July 26, 1988
INVENTOR(S) : WANG

It is certified that error appears in the above-identified patent and that said Letters Patent is hereby corrected as shown below:

IN THE TITLE:

Please delete the original title and insert therefor:

--TUBULES AND METHODS FOR SEPARATING SPERMATOZOA FROM MICROORGANISMS--

Signed and Sealed this

Fourteenth Day of March, 1989

Attest:

DONALD J. QUIGG

Attesting Officer

Commissioner of Patents and Trademarks